(12) United States Patent
Stein et al.

(10) Patent No.: US 9,810,663 B2
(45) Date of Patent: Nov. 7, 2017

(54) DEVICES AND METHODS FOR CONTAINING MOLECULES

(71) Applicant: Brown University, Providence, RI (US)

(72) Inventors: Derek M. Stein, Boston, MA (US); Xu Liu, Santa Cruz, CA (US); Mirna Mihovilovic Skanata, New York, NY (US)

(73) Assignee: Brown University, Providence, RI (US)

( * ) Notice: Subject to any disclaimer, the term of this patent is extended or adjusted under 35 U.S.C. 154(b) by 384 days.

(21) Appl. No.: 14/605,626

(22) Filed: Jan. 26, 2015

(65) Prior Publication Data
US 2016/0216234 A1 Jul. 28, 2016
US 2017/0176383 A9 Jun. 22, 2017

(51) Int. Cl.
| | | |
|---|---|---|
| *G01N 27/447* | (2006.01) | |
| *C12N 15/10* | (2006.01) | |
| *C12Q 1/68* | (2006.01) | |
| *G01N 33/487* | (2006.01) | |

(52) U.S. Cl.
CPC ..... *G01N 27/44791* (2013.01); *C12N 15/101* (2013.01); *C12Q 1/6825* (2013.01); *G01N 33/48721* (2013.01)

(58) Field of Classification Search
CPC .............................................. G01N 33/48721
See application file for complete search history.

(56) References Cited

U.S. PATENT DOCUMENTS

| | | | | |
|---|---|---|---|---|
| 6,635,163 B1 * | 10/2003 | Han | ...................... | B01D 57/02 204/450 |
| 8,586,301 B2 * | 11/2013 | Kokoris | ............... | C12Q 1/6825 435/6.1 |
| 9,085,120 B2 * | 7/2015 | Astier | ................ | G01N 27/4145 |
| 9,188,563 B2 * | 11/2015 | Mohammadi | ...... | G01N 27/4145 |

(Continued)

OTHER PUBLICATIONS

Langecker et al., Electrophoretic time-of-flight measurements of single DNA molecules with two stacked nanopores. Nano Lett. Nov. 9, 2011;11(11):5002-7. doi: 10.1021/nl2030079. Epub Oct. 13, 2011.

(Continued)

*Primary Examiner* — Alexander Noguerola
(74) *Attorney, Agent, or Firm* — Wolf, Greenfield & Sacks, P.C.

(57) ABSTRACT

The present invention generally relates to devices and methods for containing molecules. In some embodiments, the device comprises a nanopore, a pore, and a cavity capable of entropically containing (e.g., trapping) a molecule (e.g., a biomolecule), e.g., for minutes, hours, or days. In certain embodiments, the method comprises urging a molecule into a cavity of a device by application of an electric field, and/or by deposition of fluids having different ionic strengths. The molecule may comprise, in some cases, nucleic acids (e.g., DNA). The molecule, when present in the cavity and/or the nanopore, may be capable of being analyzed, determined, or chemically modified. In some instances, a second molecule (e.g., a second molecule which interacts the first molecule) may also be urged into the cavity. In some embodiments, the interaction of the second molecule with the first molecule (e.g., the second molecule binding to or chemically modifying the first molecule) may be determined by, for example, a change in voltage measured across the device.

19 Claims, 28 Drawing Sheets

(56) References Cited

U.S. PATENT DOCUMENTS

2009/0136958 A1* 5/2009 Gershow .............. C12Q 1/6825
                                                   435/6.13
2010/0243449 A1* 9/2010 Oliver ................... B82Y 30/00
                                                   204/450

OTHER PUBLICATIONS

Liu et al., Entropic trapping of single DNA Molecules emerging from a nanopore. Bulletin of the American Physical Society. Mar. 5, 2014. Denver, Colorado. Abstract Q11.00012.
Liu et al., Entropic cages for trapping DNA near a nanopore. Nat Commun. Feb. 4, 2015;6:6222. doi: 10.1038/ncomms7222.
Pedone et al., A pore-cavity-pore device to trap and investigate single nanoparticles and DNA molecules in a femtoliter compartment: confined diffusion and narrow escape. Nano Lett. Apr. 13, 2011;11(4):1561-7. doi: 10.1021/nl104359c. Epub Mar. 9, 2011.
Stein et al., Single-Molecule Test Tubes for Studying Chemical Interactions with DNA. Nanofluidics in Phy and Bio. Oct. 29-31, 2014. CECAM-HQ-EPFL. Lausanne, Switzerland. Abstract.

* cited by examiner

DEVICES AND METHODS FOR CONTAINING MOLECULES

GOVERNMENT FUNDING

This invention was made with Government support under Grant No. CBET0846505 awarded by the National Science Foundation. The Government has certain rights in this invention.

FIELD OF THE INVENTION

The present invention generally relates to devices and methods for containing molecules.

BACKGROUND

A nanometer-scale pore can be used to determine a single molecule as it passes through the pore. Nanopore sensors have, for instance, have allowed fundamental studies on single biopolymers and have shown promise in a variety of biosensing applications. Nanopores can probe chemical interactions between DNA and other molecules because these interactions often substantially modify the structure of a DNA molecule. For example, oligonucleotide hybridization probes bind to specific DNA target sequences and create bulges that are easy to detect when they pass through a nanopore. However, additional devices and methods are still needed.

SUMMARY OF THE INVENTION

The present invention provides devices and methods for containing biomolecules.

In one aspect, devices are provided. In some embodiments, the device comprises a first layer, a second layer adjacent the first layer, and a third layer adjacent the second layer, the second layer comprising a cavity having a largest cross-sectional dimension of between about 2 microns and about 8 microns and being defined between the first layer and the third layer, wherein the first layer comprises a nanopore having a largest cross-sectional dimension of less than about 20 nm accessing the cavity, and the third layer comprises a pore having a largest cross-sectional dimension of between about 200 nm and about 6000 nm accessing the cavity.

In another aspect, methods are provided. In some embodiments, the method comprises urging, using an electric field, a molecule into a cavity within a device, the cavity having a volume of between about 1 cubic micrometers and about 15 cubic micrometers, wherein in the absence of the electric field, the molecule is entropically contained within the cavity.

In some embodiments, the method comprises contacting a first fluid having a first ionic strength with a first surface of a device, wherein the first fluid comprises a molecule, contacting a second fluid having a second ionic strength with a second surface of the device such that the molecule is urged into a cavity within the device, the cavity having a volume of between about 1 cubic micrometers and about 15 cubic micrometers, wherein the first ionic strength and the second ionic strength are different.

In some embodiments, the method comprises urging, using an electric field, a single nucleic acid molecule into a cavity within a device, the cavity sized to contain only the single nucleic acid molecule, wherein in the absence of the electric field, the nucleic acid molecule has a characteristic diffusion time out of the cavity of at least 1 day.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

The present invention generally relates to devices and methods for containing molecules. In some embodiments, the device comprises a nanopore, a pore, and a cavity capable of entropically containing (e.g., trapping) a molecule (e.g., a biomolecule), e.g., for minutes, hours, or days. In certain embodiments, the method comprises urging a molecule into a cavity of a device by application of an electric field, and/or by deposition of fluids having different ionic strengths. The molecule may comprise, in some cases, nucleic acids (e.g., DNA). The molecule, when present in the cavity and/or the nanopore, may be capable of being analyzed, determined, or chemically modified. In some instances, a second molecule (e.g., a second molecule which interacts the first molecule) may also be urged into the cavity. In some embodiments, the interaction of the second molecule with the first molecule (e.g., the second molecule binding to or chemically modifying the first molecule) may be determined by, for example, a change in voltage measured across the device.

In some cases, the molecule may be entropically contained or trapped within a cavity for any suitable length of time, e.g., minutes, hours, or days. The devices and methods described herein may offer, in certain embodiments, one or more advantages for trapping molecules including, but not limited to, the ability to repeatedly trap and recover the molecule, the ability to measure and determine the interaction of multiple molecules (e.g., biosensing with a variety of chemical probes, determining interactions between two or more molecules) within a device, the ability to trap biomolecules entropically (e.g., having diffusion times out of the device of greater than minutes, hours, or days), and/or measuring the properties and/or determining the structure of, a molecule before, during, and/or after the modification (e.g., chemical modification, binding to a second molecule, enzymatic degradation, etc.) of the molecule. Such devices and methods may be useful in, for example, microscopy applications (e.g., imaging of single molecules), development of single molecule reactors and reactor arrays, development of single molecule sensors and sensor arrays, and genetic and/or genomic analysis.

Figure 1A:
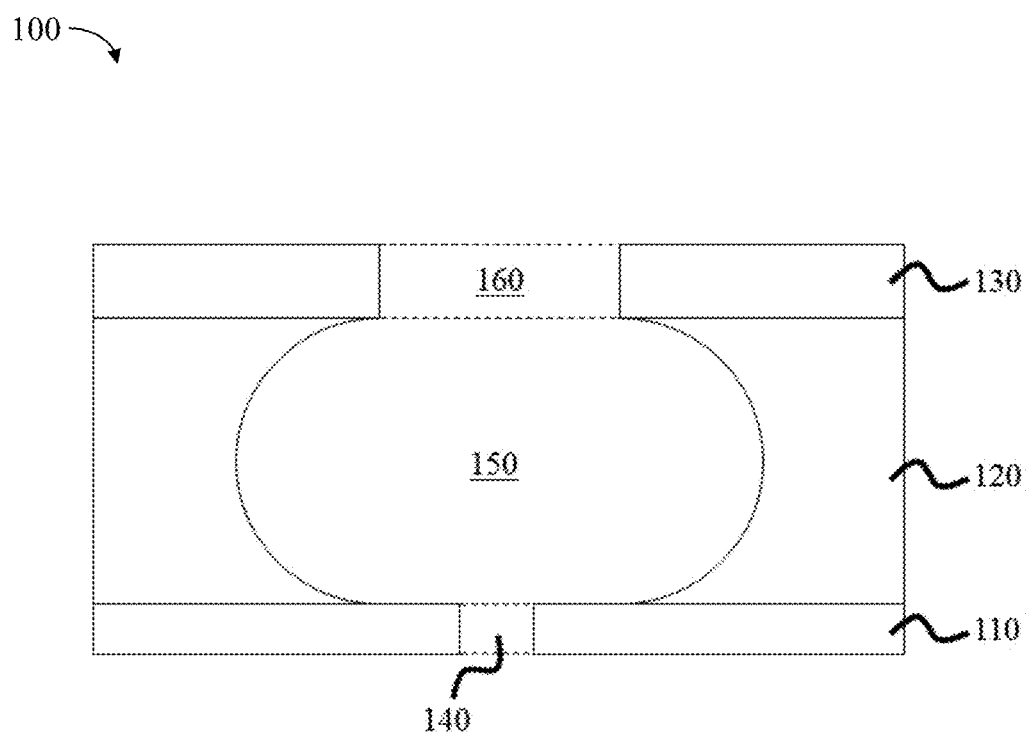
FIG. 1A-D are schematic diagrams illustrating a device comprising a cavity, according to one set of embodiments.

As illustrated in FIG. 1A, in some embodiments, device 100 comprises first layer 110, second layer 120 adjacent the first layer, and third layer 130 adjacent the second layer. In certain embodiments, first layer 110 comprises nanopore 140. In some embodiments, second layer 120 comprises cavity 150, for example, having at least one surface defined by first layer 110 and/or third layer 130, although this is not a requirement). In certain embodiments, third layer 130 comprises pore 150.

The cavity may be of any suitable shape. In some embodiments, the shape is defined by the cavity in the second layer, the first layer (e.g., comprising the nanopore), and/or the third layer (e.g., comprising the pore), although in other embodiments, the cavity is not necessarily defined in such a fashion. In some embodiments, the cavity is ellipsoidal. The term "ellipsoidal" generally refers to a geometric shape that resembles a flattened sphere has at least one cross-section that is an ellipse or a circle. In some cases, the cavity may be a capsule shape (e.g., as illustrated in FIG. 1A). The term "capsule" generally refers to a geometric shape comprising a cylinder with hemispherical ends. In some cases, the cavity may be spherical. Those skilled in the art will understand that the cavity may include one or more surfaces that are flat (e.g., as defined by the first layer and/or the third layer), are substantially non-ellipsoidal, and/or are substantially non-capsule. That is to say, in some cases, the cavity may substantially resemble an ellipsoid, sphere, or capsule in shape or overall appearance, but may not have geometric parameters which would exactly mathematically define the ellipsoid, sphere, or capsule (e.g., as a result of manufacturing methods or other practical realities). For instance, at very small length scales, there may be uncertainties or difficulties in the manufacturing or production of a cavity having dimensions on the order of nanometers, or less than one micrometer, which would prevent exact mathematical production of a cavity. In addition, other cavity shapes are possible, e.g., cubes or blocks.

In some embodiments, the cavity has a largest cross-sectional dimension, e.g., internal to the cavity. Those skilled in the art would be capable of selecting or determining an appropriate cavity size (e.g., largest cross-sectional dimension), for example, depending on the size (e.g., largest cross-sectional dimension) of one or more molecules that are desired to be entropically contained or trapped within the cavity. In some embodiments, the cavity has a largest cross-sectional dimension ranging between about 1 micron and about 8 microns. In certain embodiments, the cavity has a largest cross-sectional dimension of at least about 100 nm, at least about 300 nm, at least about 1 micron, at least about 2 microns, at least about 3 microns, at least about 4 microns, at least about 5 microns, at least about 6 microns, or at least about 7 microns. In some embodiments, the cavity has a largest cross-sectional dimension of less than or equal to about 8 microns, less than or equal to about 7 microns, less than or equal to about 6 microns, less than or equal to about 5 microns, less than or equal to about 4 microns, less than or equal to about 3 microns, less than or equal to about 2 microns, less than or equal to about 1 micron, or less than or equal to about 300 nm. Combinations of the above-referenced ranges are also possible (e.g., between about 1 microns and about 8 microns, between about 3 microns and about 7 microns, between about 2 microns and about 6 microns). Other ranges are also possible.

In certain embodiments, the cavity has a particular volume. For example, in some cases, the cavity may have a volume between about 1 cubic micron and about 15 cubic microns. In some embodiments, the cavity has a volume of at least about 1 cubic micron, at least about 2 cubic microns, at least about 5 cubic microns, at least about 7 cubic microns, at least about 10 cubic microns, or at least about 12 cubic microns. In certain embodiments, the cavity has a volume of less than or equal to about 15 cubic microns, less than or equal to about 12 cubic microns, less than or equal to about 10 cubic microns, less than or equal to about 7 cubic microns, less than or equal to about 5 cubic microns, or less than or equal to about 2 cubic microns. Combinations of the above referenced ranges are also possible (e.g., between about 1 cubic micron and about 15 cubic microns). Other ranges are also possible.

The nanopore generally has, in some instances, a largest cross-sectional dimension of less than about 20 nanometers (e.g., the nanopore accessing the cavity). Those skilled in the art would be capable of selecting an appropriate nanopore size (e.g., a largest cross-sectional dimension) such that one or more molecules contained within the cavity diffuse through the nanopore with a characteristic diffusion time out of the nanopore of at least minutes, hours, or days, as described in more detail below. In some embodiments, the nanopore has a largest cross-sectional dimension of less than about 20 nanometers, less than about 15 nanometers, less than about 12 nanometers, less than about 10 nanometers, less than about 9 nanometers, less than about 8 nanometers, less than about 6 nanometers, less than about 5 nanometers, less than about 3 nanometers, or less than about 2 nanometers.

In some embodiments, the nanopore has a particular volume, for instance, as defined by the surface at which the nanopore accessing the cavity and the opposing surface of the first layer, as illustrated in FIG. 1A. In some embodiments, the nanopore has a volume of less than about 6000 cubic nanometers. In certain embodiments, the nanopore has a volume of less than about 5000 cubic nanometers, less than about 4000 cubic nanometers, less than about 3000 cubic nanometers, less than about 2000 cubic nanometers, less than about 1000 cubic nanometers, or less than about 500 cubic nanometers.

The pore, in one set of embodiments, has a largest cross-sectional dimension of between about 200 nanometers and about 6000 nanometers. The pore and the nanopore may independently be of the same or different shapes or sizes. Those skilled in the art would be capable of selecting an appropriate pore size depending on the size of the one or more molecules desired to pass through the pore and enter the cavity, for instance, such that the one or more molecules are entropically contained or trapped within the cavity. In some cases, the molecules are sterically hindered or physical restrained within the cavity, e.g., such that the cavity restricts the motion of the molecule within the cavity. This may slow down and/or prevents the diffusion of the molecule out of the cavity. In some embodiments, the pore has a largest cross-sectional dimension of at least about 200 nanometers, at least about 300 nanometers, at least about 400 nanometers, at least about 500 nanometers, at least about 1000 nanometers, at least about 2000 nanometers, at least about 4000 nanometers, or at least about 5000 nanometers. In certain embodiments, the pore has a largest cross-sectional dimension of less than or equal to about 6000 nanometers, less than or equal to about 5000 nanometers, less than or equal to about 4000 nanometers, less than or equal to about 2000 nanometers, less than or equal to about 1000 nanometers, less than or equal to about 500 nanometers, less than or equal to about 400 nanometers, or less than or equal to about 300 nanometers. Combinations of the above referenced ranges are also possible (e.g., between about 200 nanometers and about 6000 nanometers, between about 200 nanometers and about 2000 nanometers, between about 200 nanometers and about 500 nanometers). Other ranges are also possible.

In some embodiments, the pore has a particular volume. For example, in some instances, the volume of the pore may range between about 0.01 cubic microns and about 10 cubic microns. In some embodiments, the volume of the pore is at least about 0.01 cubic microns, at least about 0.02 cubic microns, at least about 0.05 cubic microns, at least about 0.1 cubic microns, at least about 0.2 cubic microns, at least about 0.5 cubic microns, at least about 1 cubic microns, at least about 2 cubic microns, or at least about 5 cubic microns. In certain embodiments, the volume of the pore is less than or equal to about 10 cubic microns, less than or equal to about 5 cubic microns, less than or equal to about 2 cubic microns, less than or equal to about 1 cubic microns, less than or equal to about 0.5 cubic microns, less than or equal to about 0.2 cubic microns, less than or equal to about 0.1 cubic microns, less than or equal to about 0.05 cubic microns, or less than or equal to about 0.02 cubic microns. Combinations of the above-referenced ranges are also possible (e.g., between about 0.01 cubic microns and about 10 cubic microns). Other ranges are also possible.

In some embodiments, the pore, nanopore, and cavity form a fluidic pathway. For example, in some embodiments, a fluid can flow through the pore into the cavity and out of the nanopore, or vice versa. In some embodiments, the pore, nanopore, and cavity are substantially aligned. For example, in some cases, a straight line can be drawn through both the nanopore and the pore without containing any of the first layer, the second layer, or the third layer. However, it should be understood that in other embodiments, the pore, nanopore, and cavity need not be substantially aligned.

Figure 1B:
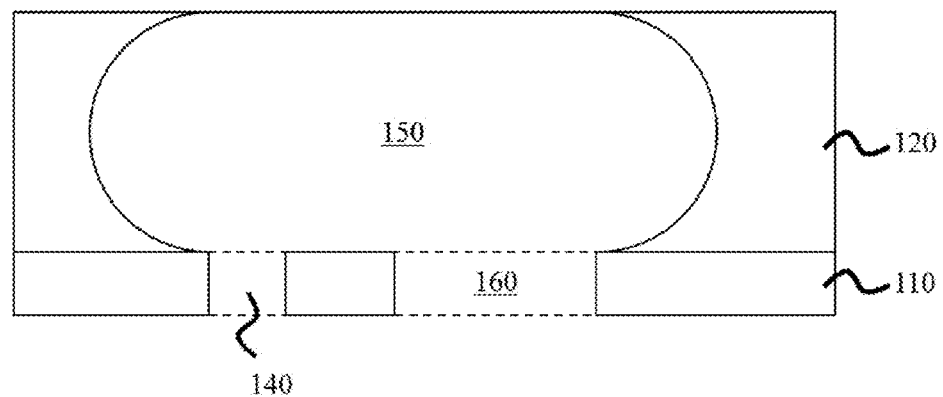
Figure 1C:
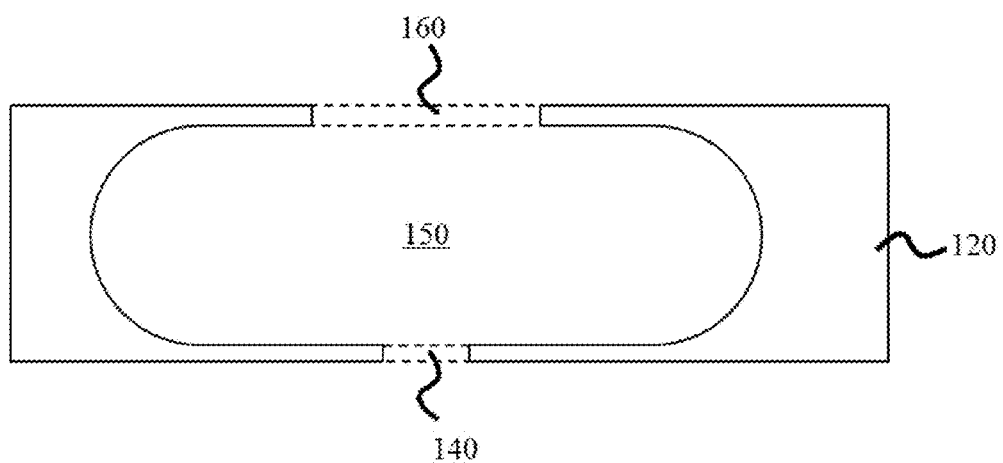
Figure 1D:
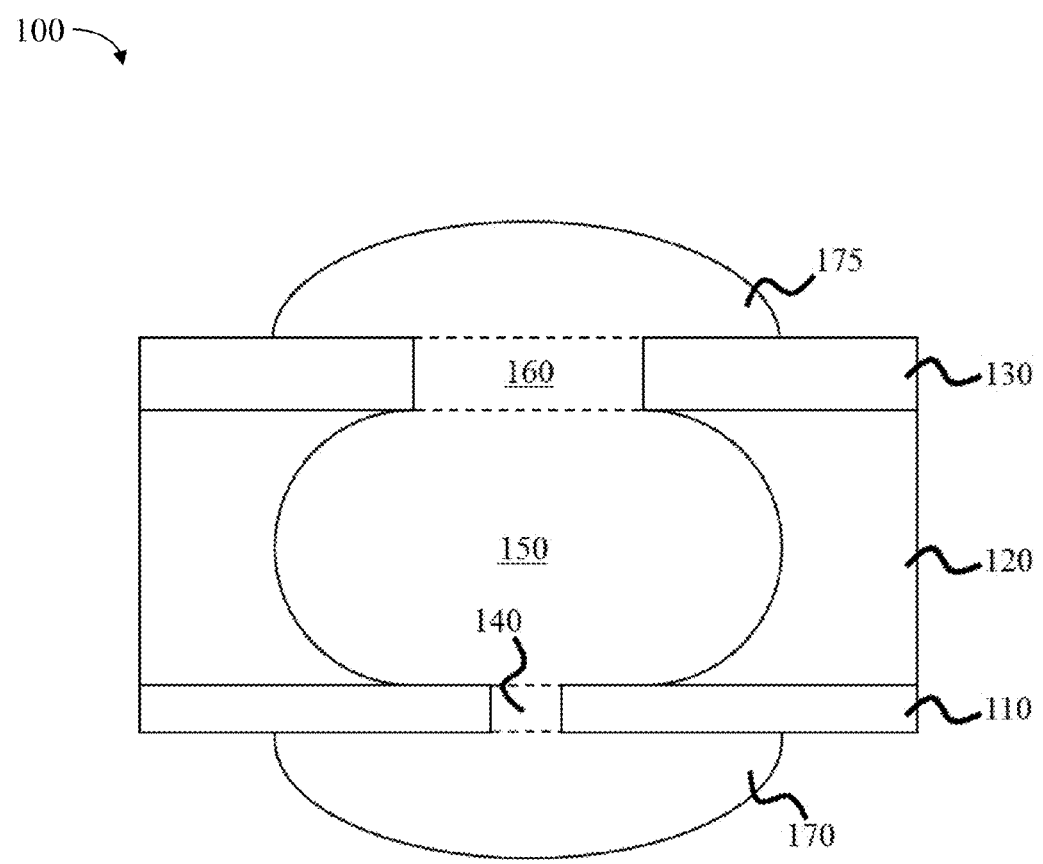

In some embodiments, the pore, nanopore, and/or cavity may be in different layers of a device, as was illustrated in FIG. 1A. However, in other embodiments, the nanopore, pore, and/or cavity may be present in the same layer, or there may be more or fewer layers present (or even only a single material or layer, in some cases). For example, referring to FIG. 1B, in certain embodiments, device 100 comprises first layer 110 comprising nanopore 140 and pore 160, and second layer 120 adjacent the first layer comprising cavity 150 (e.g., having at least one surface defined by first layer 110, although this is not a requirement). Referring now to FIG. 1C, as yet another example, in some embodiments, device 100 comprises layer 120 comprising nanopore 140, pore 160, and cavity 150. Other configurations are also possible.

The first layer may generally comprise any suitable material. For example, in some embodiments, the first layer (e.g., the first layer comprising the nanopore) comprises a dielectric material, such as silicon nitride. Those skilled in the art would be capable of selecting other appropriate materials (e.g., suitable for manufacturing a nanopore, as described herein, therein) for making devices comprising a nanopore and a cavity, as described herein. Other examples of dielectric materials that could be used include, but are not limited to, semiconductor oxides or metal oxides such as $SiO_2$, $GeO_2$, $SeO_2$, $SnO_2$, $GaO_2$, $TiO_2$, $Al_2O_3$, $HfO_2$, $NiO_2$, $NiO$, $BaTiO_3$, $SrTiO_3$, $Fe_3O_4$, $Fe_2O_3$, $MgO$, $Cr_2O_3$, $ZnO$, $MgO$, $VO_2$, $V_2O_5$, $MnO$, $CO_2O_3$, $CO_3O_4$, $CuO$, $Cu_2O$, $ZrO_2$, $BaO$, $WO_2$, $CeO_2$, and the like; nitrides such as silicon nitride, boron nitride, titanium nitride, gallium nitride, indium nitride, aluminum nitride, and the like; and carbines such as silicon carbide, tungsten carbine, boron carbide, magnesium carbide, and the like. In some embodiments, the first layer may comprise monolayer-thin materials such a graphene, hexagonal boron nitride, or the like. In certain embodiments, the first layer may comprise diamond. In some cases, the first layer may comprise a semiconducting material such as silicon, gallium arsenide, or the like; conducting materials such as gold, silver, platinum, copper, or the like; or polymers such as polyamides, or the like. In some embodiments, the first layer may comprise combinations of and/or one or more layers of one or more suitable materials described above.

In some embodiments, the first layer has a particular thickness. For example, in some cases, the thickness of the first layer may range between about 10 nanometers and about 50 nanometers. In some embodiments, the thickness of the first layer is greater than or equal to about 10 nanometers, greater than or equal to about 20 nanometers, greater than or equal to about 30 nanometers, or greater than or equal to about 40 nanometers. In certain embodiments, the thickness of the first layer is less than about 50 nanometers, less than about 40 nanometers, less than about 30 nanometers, or less than about 20 nanometers. Combinations of the above referenced ranges are also possible (e.g., between about 10 nanometers and about 50 nanometers, between about 10 nanometers and about 30 nanometers).

The third layer (if present) may generally comprise any suitable material. In some embodiments, the first layer and the third layer comprise the same material. In certain embodiments, the first layer and the third layer comprise different materials. In some embodiments, the third layer (e.g., the third layer comprising the pore) comprises silicon nitride, or other dielectric materials such as those described above. Those skilled in the art would be capable of selecting other appropriate materials (e.g., suitable for manufacturing a pore, as described herein, therein) for making devices comprising a pore and a cavity, as described herein.

In some embodiments, the third layer has a particular thickness. For example, in some cases, the thickness of the third layer may range between about 100 nanometers and about 1000 nanometers. In some embodiments, the thickness of the third layer is greater than or equal to about 100 nanometers, greater than or equal to about 200 nanometers, greater than or equal to about 400 nanometers, greater than or equal to about 600 nanometers, or greater than or equal to about 800 nanometers. In certain embodiments, the thickness of the third layer is less than about 1000 nanometers, less than about 800 nanometers, less than about 600 nanometers, less than about 400 nanometers, or less than about 200 nanometers. Combinations of the above referenced ranges are also possible (e.g., between about 100 nanometers and about 1000 nanometers, between about 100 nanometers and about 600 nanometers, between about 200 nanometers and about 600 nanometers). Other ranges are also possible. The third layer may have the same or a different thickness than the first layer.

The second layer (if present) may generally comprise any suitable material. In some embodiments, the second layer (e.g., the second layer comprising the cavity) comprises silicon dioxide, a dielectric material, monolayer-thin materials, a semiconducting material, a conducting material, diamond, or polymers such as those given above. Those skilled in the art would be capable of selecting other appropriate materials (e.g., suitable for manufacturing a cavity, as described herein, therein) for making devices comprising a nanopore, a pore, and a cavity, as described herein. The materials of the second layer may be the same or different than the materials of the first layer and/or the third layer.

In some embodiments, the second layer has a particular thickness. In certain embodiments, the thickness of the second layer (e.g., the second layer comprising the cavity) is between about 0.5 microns and about 5 microns. In some cases, the thickness of the second layer may be at least about 0.5 microns, at least about 1 micron, at least about 2 microns, or at least about 4 microns. In certain embodiments, the thickness of the second layer is less than or equal to about 5 microns, less than or equal to about 4 microns, less than or equal to about 2 microns, or less than or equal to about 1 micron. Combinations of the above-referenced ranges are also possible (e.g., between about 0.5 microns and about 5 microns, between about 0.5 microns and about 2 microns). Other ranges are also possible.

In some embodiments, the device comprises one or more additional substrates or layers (e.g., a membrane, a support, etc.). In some embodiments, for instance, one or more of the substrates or layers may comprise silicon or other suitable materials, e.g., including those discussed herein.

In certain embodiments, the device also comprises one or more fluid layers. As illustrated in FIG. 1C, in some embodiments, the device comprises first fluid layer 170 comprising a first fluid adjacent first layer 110. In some such embodiments, the first fluid may flow into nanopore 140, cavity 150 and/or pore 160. In certain embodiments, the device comprises second fluid layer 175 comprising a second fluid adjacent second layer 130. In some such embodiments, the second fluid may flow into pore 160, cavity 150, and/or nanopore 140. In some cases, the first fluid and the second fluid may mix, e.g., within the cavity. In certain embodiments, a concentration gradient of a particular ion and/or molecule may be present between the first fluid and the second fluid across the device, e.g., through the cavity. For example, in some embodiments, the first fluid may comprise a first concentration of a molecule and the second fluid may comprise a second concentration of the molecule. In some embodiments, the first concentration and the second concentration may be different. In some cases, the first concentration of the molecule (e.g., the concentration of the molecule present in the first fluid) is about zero. Thus, in some embodiments, the difference in concentration (e.g., a concentration gradient) of a molecule between the first fluid and the second fluid may cause the molecule to flow into the pore and/or the cavity towards the nanopore. In certain embodiments, the molecule may have a largest cross-sectional dimension such that it can not readily pass through the nanopore in the absence of an external force, such as an electric field or a concentration gradient (e.g., the molecule is trapped within the cavity). In some embodiments, the molecule may be capable of passing through the nanopore, but with a diffusion or characteristic time of minutes, hours, or days. For example, a molecule contained within the cavity may exit via diffusion, but the characteristic or average time for the molecule to passively diffuse out of the cavity, e.g., through a pore or nanopore, may be on the order of minutes, hours, or even days in some cases. Under such conditions, the molecule may be considered to be entropically contained within the cavity. Molecules (e.g., biomolecules) for use in the device are described in more detail, below.

In some embodiments, one or more of the fluids (e.g., the first fluid, the second fluid) comprise a salt. Non-limiting examples of suitable salts including, for example, sodium chloride, potassium chloride, and lithium chloride.

In certain embodiments, one or more of the fluids comprise an ionic buffer. In some cases, the ionic buffer comprises tris(hydroxymethyl)aminomethane (tris), ethylenediaminetetraacetic acid, potassium acetate, tris-acetate, magnesium acetate, dithiothreitol, or the like. Other examples include phosphate-buffered saline or cell media. Those skilled in the art would be capable of selecting suitable additional ionic buffers for use in the device and methods described herein.

In certain embodiments, one or more of the fluids may have a particular ionic strength. For example, in some cases, the first fluid may have a first ionic strength and the second fluid may have a second ionic strength. In some such embodiments the first ionic strength and the second ionic strength may be different. In some embodiments, the difference in ionic strength between the first fluid and the second fluid is at least about 10%, relative to the smaller ionic strength of the two fluids. The difference may also be at least about 20%, at least about 30%, at least about 40%, or at least about 50%. In some cases, the difference may also be at least about 100%, at least about 1,000%, at least about 10,000%, or at least about 100,000%. Those skilled in the art would be capable of selecting appropriate differences in ionic strengths based upon the teachings of this specification.

In some embodiments, the one or more fluids may have an ionic strength ranging between about 0.1 micromolar and about 4 M. For example, in some embodiments, the first fluid may have a first ionic strength of between about 10 mM and about 4 M, and the second fluid may have a second ionic strength between about 0.1 micromolar and about 100 mM. In some embodiments, the one or more fluids may have an ionic strength of at least about 0.1 micromolar, at least about 1 micromolar, at least about 10 micromolar, at least about 50 micromolar, at least about 100 micromolar, at least about 500 micromolar, at least about 1 mM, at least about 5 mM, at least about 10 mM, at least about 50 mM, at least about 100 mM, at least about 500 mM, or at least about 1M. In certain embodiments, the one or more fluids may have an ionic strength of less than or equal to about 4 M, less than or equal to about 1 M, less than or equal to about 500 mM, less than or equal to about 100 mM, less than or equal to about 50 mM, less than or equal to about 10 mM, less than or equal to about 1 mM, less than or equal to about 500 micromolar, less than or equal to about 100 micromolar, less than or equal to about 50 micromolar, less than or equal to about 10 micromolar, less than or equal to about 5 micromolar, or less than or equal to about 1 micromolar. Combinations of the above-referenced ranges are also possible (e.g., between about 0.1 micromolar and about 100 mM, between about 10 mM and about 4 M). Other ranges are also possible. Those skilled in the art would be capable of selecting appropriate methods for determining ionic strength of a fluid.

In some embodiments, one or more of the fluids comprises one or more molecules (e.g., the molecule to be contained within the cavity). In certain embodiments, the one or more molecules is a biomolecule. Suitable biomolecules for trapping within a cavity include, for example, nucleic acids (e.g., DNA, RNA). In some such embodiments, the nucleic acids may have any suitable length. For example, in some embodiments, the nucleic acid is between 1-100 nucleotides, between 100-1,000 nucleotides, between 1,000-10,000 nucleotides, between 10,000-50,000 nucleotides, between 10,000-100,000 nucleotides, between 50,000-100,000 nucleotides, between 100,000-1,000,000 nucleotides, between 50,000-5,000,000 nucleotides, or greater than 5,000,000 nucleotides (e.g., between 5,000,000 and 500,000,000 nucleotides) in length. In some embodiments, the nucleic acids may be relatively short chains (e.g., fragments) or may be relatively long chains (e.g., the length of a gene, the length of at least a portion of a chromosome, the length of an entire chromosome such as human chromosome 1). Other lengths are also possible.

In some embodiments, the fluid comprises a first molecule (e.g., the nucleic acid) and a second molecule capable of interacting with the first molecule. For instance, the second molecule may be able to bind to (covalently, ionically, through van der Waals or hydrogen bonding, etc.), chemically modify, or react with the first molecule. In some embodiments, the second molecule capable of interacting with the first molecule comprises an enzyme, a protein, an oligonucleotide (e.g., an oligonucleotide hybridization probe), or the like. In some cases, the second molecule capable of interacting with the first molecule comprises a compound capable of chemically modifying nucleic acids (e.g., compounds that cleave, methylate, demethylate, phosphorylate, dephosphorylate, hydrosylate, glycosylate, deglycosylate, acetylate, deacetylation, oxidate, alkylate, bind, or act carcinogenically (e.g., carbon electrophiles)). In some such embodiments, the first molecule (e.g., a biomolecule such as a nucleic acid) may be contained within the cavity and the second molecule capable of interacting with the first molecule may enter the cavity and interact with the first molecule In some embodiments, a molecule may have a particular cross-sectional dimension. For example, in some cases, the cross-sectional dimension may be small enough such that the molecule can pass through the pore and enter the cavity, but large enough that it can not pass through the nanopore. In certain embodiments, the size (e.g., cross-sectional dimension, volume) of the pore, nanopore, and/or cavity may be selected based upon the size (e.g., the cross-sectional dimension) of the desired one or more molecules to be entropically contained or trapped within the cavity. In some embodiments, the first molecule may be entropically contained or trapped within the cavity and the second molecule may be free to flow out of the cavity (e.g., via the pore).

The pore, nanopore, and/or cavity can be fabricated by any suitable method. For example, in some embodiments, the pore, nanopore, and/or cavity may be fabrication via techniques such as micromachining, photolithography, e-beam lithography, or the like. In some embodiments, for example, the pore (e.g., in the third layer) may be formed via ion beam milling, for instance, using a focused ion beam or other suitable techniques. In certain embodiments, the cavity (e.g., in the second layer) may be formed (e.g., after forming the pore) via etching using techniques such as HF etching or the like. In some such embodiments, the duration of etching may determine the size or largest cross-sectional dimension of the cavity. In certain embodiments, the nanopore may be formed via transmission electron microscopy milling, for instance, using a focused beam via a transmission electron microscope. In some cases, the first layer, the second layer, and the third layer may be assembled prior to the formation of the pore, nanopore, and/or cavity. Those skilled in the art would be capable of selecting additional suitable methods for fabricating the device, as described herein.

In some embodiments the device comprises a voltage source, which may be used to produce an electric field across the device, or portion thereof. Such electric fields may be used to urge a molecule into the pore and/or the cavity.

A device as described herein may, in some cases, be able to contain or trap a molecule for minutes, hours, or days, e.g., as compared to seconds. For instance, in some embodiments, a method as described herein comprises trapping or entropically containing one or more molecules within the cavity, for example, via electric field, via concentration gradient, or the like. For example, an electric field may be used to move a molecule into a cavity within a device, wherein in the absence of the electric field, the molecule is entropically contained within the cavity. Thus, in some cases, after the application of the electric field (i.e. the voltage source is turned off), the molecule may be contained within the cavity for a significant amount of time.

Referring again to FIG. 1C, in some embodiments, the method comprises contacting first fluid 170 having a first ionic strength with the first layer 110 of a device (e.g., comprising nanopore 140), contacting second fluid 175 having a second ionic strength with the third layer 130 of the device (e.g., comprising pore 160), as described above, such that the molecule is urged into cavity 150 within the device. The molecule contained within the cavity may have a particular diffusion time. In some embodiments, the diffusion time is on the order of minutes, hours, or days. For example, in some cases, the molecule may be trapped within the cavity for a diffusion time of at least about a minute, at least about 10 minutes, at least about 30 minutes, at least about an hour, at least about 6 hours, or at least about 24 hours. Other diffusion times are also possible.

In some embodiments, a reaction involving a molecule contained within a cavity may be determined. For example, one or more properties of the molecule may be measured or otherwise determined before, during, and/or after a reaction, e.g., by measuring the voltage across the device before, during, and/or after the reaction. In some embodiments, the device herein may be useful for analysis, determination, and/or measurement methods of molecules and their interaction and/or binding partners. In one such embodiment, as described above the molecule may comprise a nucleic acid, such as DNA or RNA. The presence of DNA may, for example, reduce the current measured across the device to a first current, and the presence of DNA bound to a second molecule may further reduce the current measured across the device to a second current ("DNA bar-reading").

Such devices may be useful for, for example, measuring length of DNA or RNA or other nucleic acids, direct sequencing of nucleic acids, determining binding of proteins, enzymes, or other analytes to specific sequences (e.g., biomarker detection), and restriction analysis.

These and other aspects of the present invention will be further appreciated upon consideration of the following Examples, which are intended to illustrate certain particular embodiments of the invention but are not intended to limit its scope, as defined by the claims.

Example 1

The following example describes the fabrication of a nanopore/cavity device, according to some embodiments.

Figure 2:
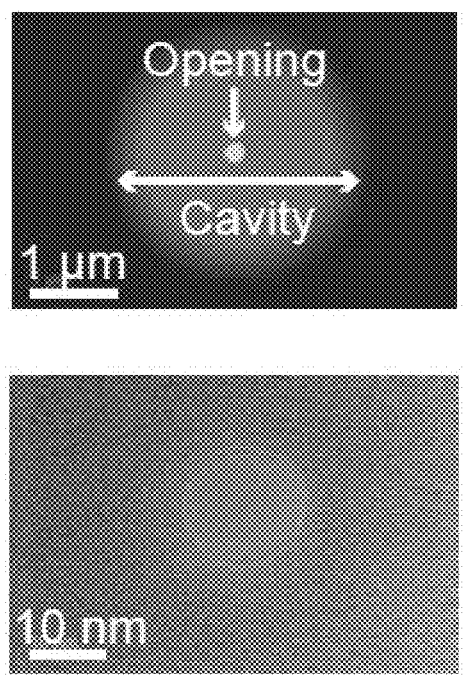
FIG. 2 is a transmission electron microscopy image of the pore (opening, top) and nanopore (bottom).

Each structure in this example was made in a freestanding membrane on a silicon chip. Silicon chips with freestanding membranes suspended over 50 micron wide square openings were microfabricated by standard procedures known in the art. The membrane comprised a S-layer stack of materials. The outermost layer, made of low-stress silicon nitride, was about 20 nm thick. The middle layer was about 1.5 microns thick and made of silicon dioxide. The layer closest to the silicon chip was about 400 nm thick and made of low-stress silicon nitride. To create the nanopore-cage structures, a focused ion beam machine (FIB, FEI Helios) was used to mill a 200 nm diameter opening through the innermost layer of silicon nitride. A buffered HF etch then selectively removed $SiO_2$ from the middle layer, creating a 1.5 micron-high cavity whose diameter was selected by controlling the duration of the etch. A diameter of 2.3 microns was obtained after 10 min of etching. The cavity was large enough to accommodate a λ-DNA (lambda DNA) molecule, which is about 16.5 microns long and has a radius of gyration that is about Rg=730 nm in equilibrium. Finally, the beam of a TEM (JEOL 2100F) was focused onto the 20 nm-thick silicon nitride layer to mill a 10 nm diameter nanopore through it. FIG. 2 is a transmission electron microscope (TEM) image of an exemplary device. Table 1 summarizes the dimensions of several exemplary devices used in Examples 2-4.

TABLE 1

| Device | Nanopore diameter (nm) | Opening diameter (nm) | Cavity diameter (microns) |
| --- | --- | --- | --- |
| 1 | 8.5 | 230 | 2.28 |
| 2 | 14.9 | 230 | 2.25 |

TABLE 1-continued

| Device | Nanopore diameter (nm) | Opening diameter (nm) | Cavity diameter (microns) |
| --- | --- | --- | --- |
| 3 | 11 | 240 | 2.3 |
| 4 | 10.2 | 1560 | 6.12 |
| 5 | 9.1 | 5320 | 7.32 |
| 6 | 9.4 | 230 | 3.3 |
| 7 | 14 | 290 | 2.72 |
| 8 | 8.7 | 240 | 2.46 |

Prior to a DNA sensing experiment, each device was cleaned in sulfuric acid and hydrogen peroxide at 75° C. for two hours, and its ionic conductance was tested in the presence of 1 M KCl buffer to ensure that the standard deviation of the baseline current was no greater than 0.01 nA with V=100 mV.

Example 2

The follow example describes the experimental methods used to trap and sense DNA in the nanopore/cavity devices described in Example 1.

In DNA sensing experiments, the chip separated two reservoirs of buffered ionic solution, one contacting the opening of the cavity (the "opening side"), and the other contacting the nanopore and containing λ-DNA (lambda DNA) (the "nanopore side"). The only fluidic path between the two reservoirs passed through the nanopore, the cavity and the opening. An electrometer biased the opening side to a voltage, V relative to the nanopore side and measured the resulting ionic current through the nanopore, I, by means of Ag/AgCl electrodes immersed in the reservoirs. The opening, while small enough to confine the DNA, was too large to significantly affect the ionic resistance of the device, which was governed by the nanopore. I was the basis of the sensing mechanism: DNA molecules passed through the nanopore due to electrophoresis, and the presence of a molecule inside the nanopore causes a measurable change in I. The time course of I generally relates to the structure of the molecule. A field-programmable gate array (FPGA) digitized I and enabled real-time control over V in response to changes in I or pre-programmed delays.

Figure 3A:
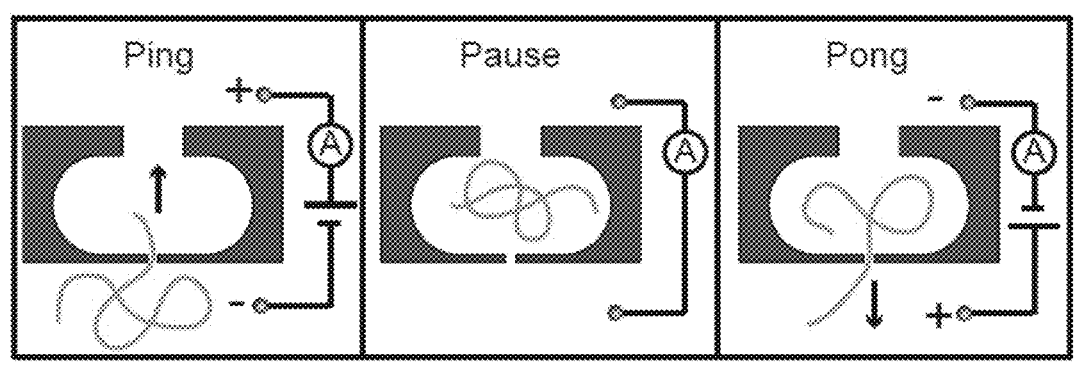
FIG. 3A is a schematic illustration of a "ping, pause, pong" experiment, according to one set of embodiments.
Figure 3B:
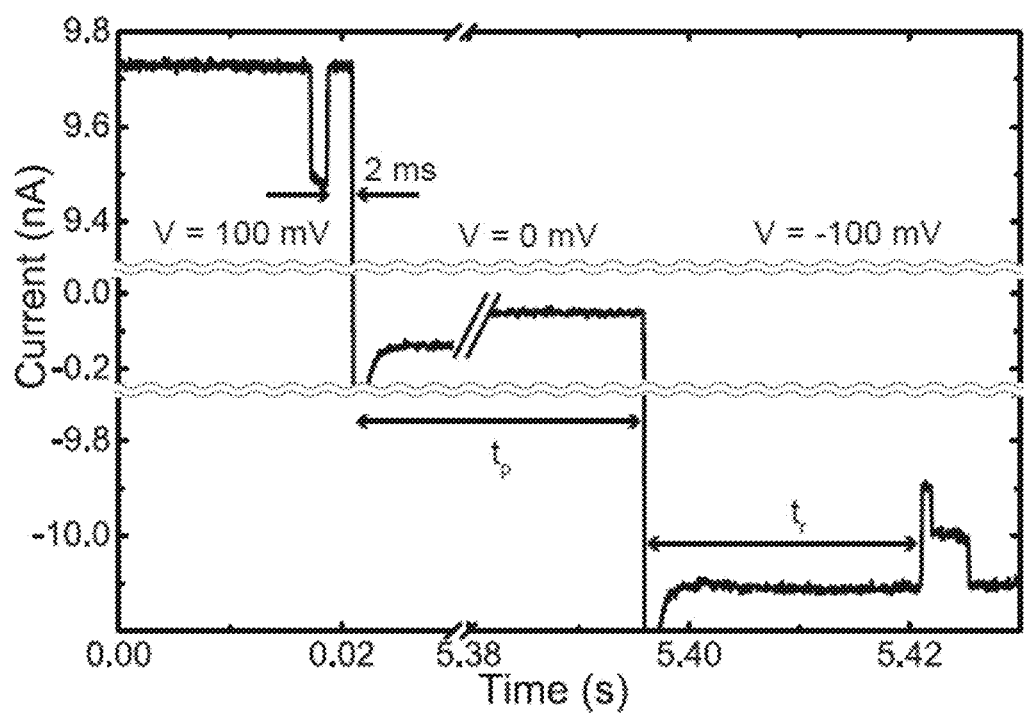
FIG. 3B is a plot of current versus time for an exemplary "ping, pause, pong" experiment.

The dynamics of the DNA molecules in the entropic cage were investigated with "ping-pause-pong" experiments, as illustrated in FIG. 3A. A current trace from an exemplary experiment is shown in FIG. 3B. The application of V=100 mV resulted in a current of 9.73 nA through the open 8.5 nm diameter pore. When a DNA molecule translocated the nanopore into the cage, it caused a transient decrease in I. This first translocation signal was labelled the "ping." The positive voltage bias was maintained for 2 ms following the ping. The voltage bias was then removed for a pause time, $t_p$, during which the molecule could relax and diffuse within the cavity. $t_p$ was varied in experiments between 2 ms and 50 s. Following the pause, the voltage was flipped to V=−100 mV for 5 s. Another transient conductance drop was frequently observed, which was labelled the "pong" and was generally attributed to the same DNA molecule returning through the nanopore. The interval of time between the voltage reversal and the pong is $t_r$, the recapture time. In these experiments, the ionic current approached a new open-pore value gradually and reproducibly following a change in voltage, whether or not a molecule had translocated the nanopore. The slow change in the baseline current corresponded to the instrumentation and the nanopore rather than the DNA. Interestingly, the course of the current baseline could be extrapolated continuously across ping and pong events, without any shift resulting from the translocation of a molecule into or out of the cage at various magnitudes of $t_p$ (See FIGS. 7A-D). The presence of a DNA molecule inside the cage had substantially no observable effect on the access resistance of the device.

Figure 4A:
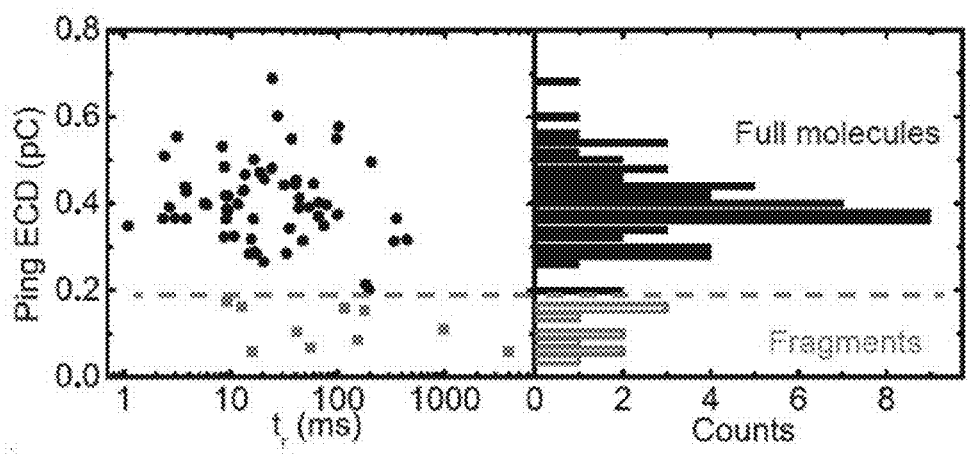
FIG. 4A is a scatter plot sowing the event charge deficit (ECD) for an exemplary set of "pings" of DNA trapped in a cavity.
Figure 4B:
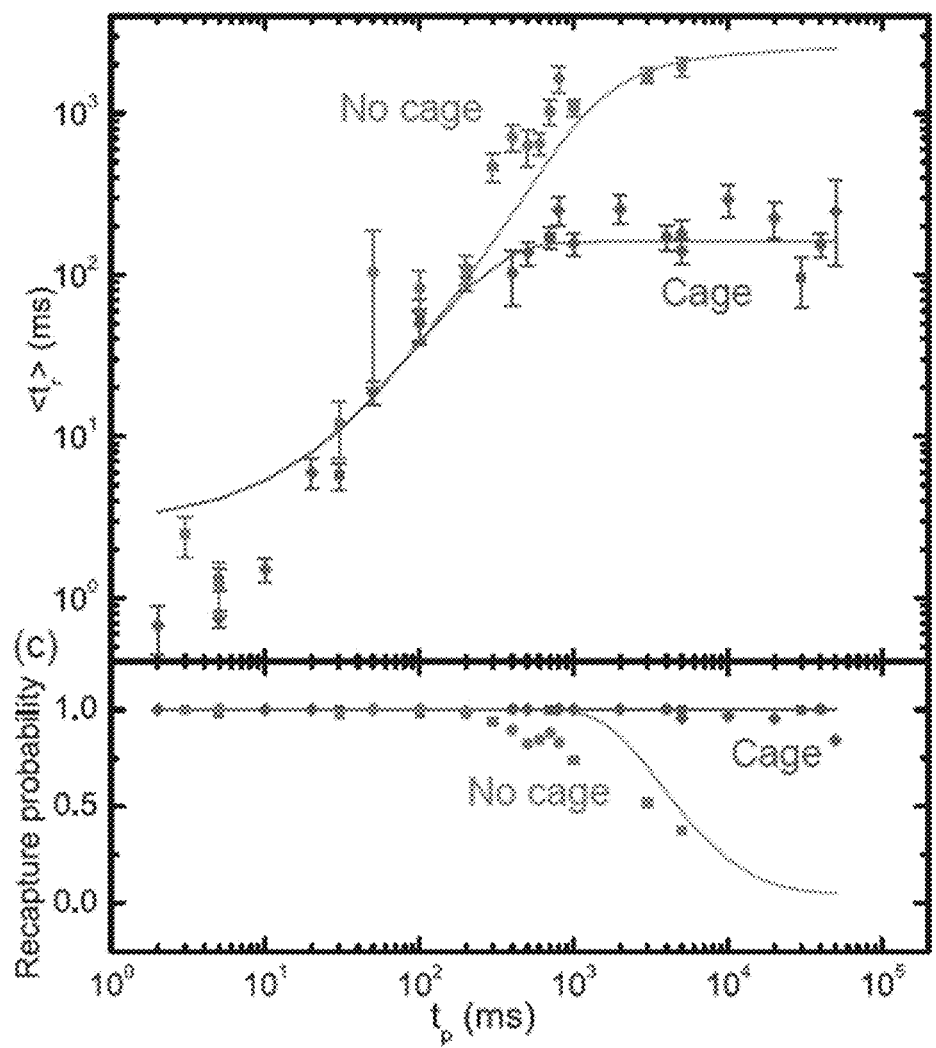
FIG. 4B is a plot of mean return time ($<t_r>$) and recapture probability as a function of time for DNA trapped in a cavity.

For each DNA translocation, the event charge deficit (ECD) was computed, which is the induced current change integrated over the duration of the event. ECD is generally related to the length of a DNA molecule and not the folding configuration in which it translocates. Since λ-DNA is generally very long, it is an excellent candidate for entropic trapping, but also relatively easy to break and difficult to purify. Consequently, nanopore studies of λ-DNA typically reveal a subpopulation of much shorter molecules (presumably fragments) which may respond differently to an entropic cage, especially if their radius of gyration is smaller than the opening. ECD was used to identify and remove short fragments of DNA from the data. FIG. 4A shows a scatter plot indicating the ECD of each ping and the corresponding $t_r$ for $t_p$=30 ms. Most of the data clustered in a major group centered around ECD=0.4 pC and $t_r$=20 ms. A small number of molecules with low ECD (~0.1 pC) were more broadly distributed in $t_r$ and a few of them exhibited extremely long return times (>1 s). FIG. 4B shows the distribution of ping ECD values, which has a major peak near 0.4 pC and a minor tail that is most prominent around 0.1 pC. The pings in the major group were generally attributed to translocations of intact DNA molecules, and those in the minor tail to shorter fragments. The threshold ECD=0.2 pC was used to distinguish between intact molecules and fragments. Experiments with different $t_p$ gave similar ping ECD distributions, where the threshold generally left the main group of translocations untouched at various values of $t_p$ (see FIGS. 8A-D). Furthermore, molecules identified as fragments based on the ping ECD resulted in low pong ECDs, as expected (see FIGS. 8A-D). Fragments comprised less than 20% of the translocations in every experiment. For the analysis which follows, only intact molecules were considered.

FIG. 4B shows the dependence of the mean return time $<t_r>$ on $t_p$. $<t_r>$ increased with $t_p$ until $t_p$~700 ms, where it saturated at $<t_r>$~250 ms (FIG. 4B, top, "Cage"). The saturation in $<t_r>$ was determined to be due to the presence of the cage by performing the following control experiments. The same ping-pause-pong procedure was applied, only this time using a device whose cavity and opening diameters (7.32 microns and 5.32 microns, respectively) were much larger than the equilibrium coil size of λ-DNA that the cavity could not impede the molecule's motion. Because of this, that device behaved as if there were no cage at all. The results of these control experiments are shown in FIG. 4B (Top, "No cage" squares). $<t_r>$ increased with $t_p$ over the full range of pause times tested. The longest pause, $t_p$=50 s, gave $<t_r>$=2 s, which was nearly an order of magnitude longer than the $t_r$ plateau value observed in experiments with a cage. Similar results were obtained using a second device with a large 6.12 micron diameter cavity and a 1.56 micron diameter opening. Those results are also shown in FIG. 4B (Top, "No cage" circles).

The cage also generally enhanced the probability of recapturing a molecule, defined as the fraction of ping-pause-pong cycles where the ping was followed by a pong. FIG. 4B (bottom) plots the dependence of the recapture probability on $t_p$ for translocations into a cage and for translocations across a device with no cage. In the absence of a cage, the recapture probability decreased precipitously with $t_p$ for $t_p$>200 ms. The longest pause in the cage-free experiments was 5 s. By contrast, the recapture probability remained high in devices with a cage, even for $t_p$=50 s (100% for two devices and >80% for a third device).

Figure 9:
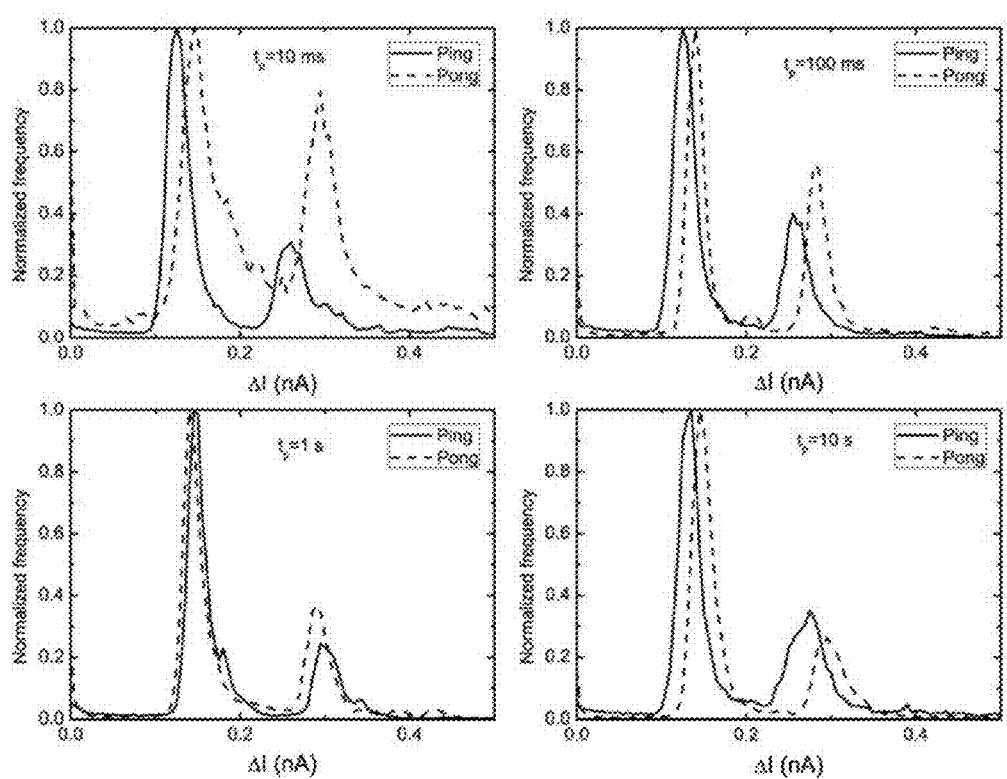
FIG. 9 are plots of change in current versus normalized density for DNA molecules trapped in a nanopore of an exemplary device.
Figure 10:
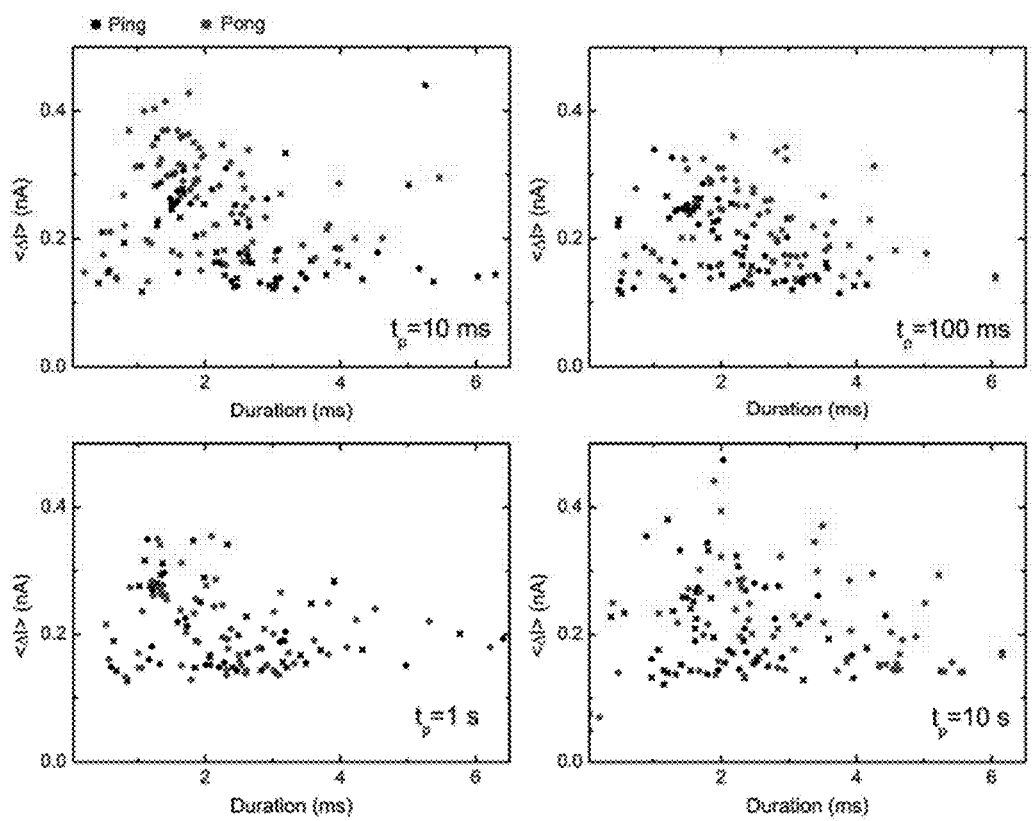
FIG. 10 are scatter plots of exemplary "ping" and "ping" events as a function of time.

Finally, translocations produced bimodal distributions of current blockage amplitudes which revealed a greater frequency of large blockages among pongs than pings, with the largest difference observed for short $t_p$ (See FIG. 9). This may be explained by DNA forming a compact coil close to the nanopore immediately after the ping, which increases the frequency of folded configurations during the pong. The difference in current blockage distributions was not accompanied by a clear difference in translocation durations between pings and pongs (see FIG. 10).

Example 3

The follow example describes the experimental methods for visualizing entropically trapped DNA in the nanopore/cavity devices described in Example 1.

Figure 5A:
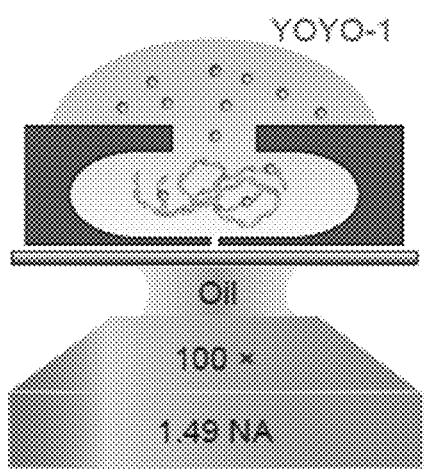
FIG. 5A is a schematic representation of imaging a DNA molecule trapped in an exemplary cavity and exposed to a dye (YOYO-1), according to one set of embodiments.
Figure 5B:
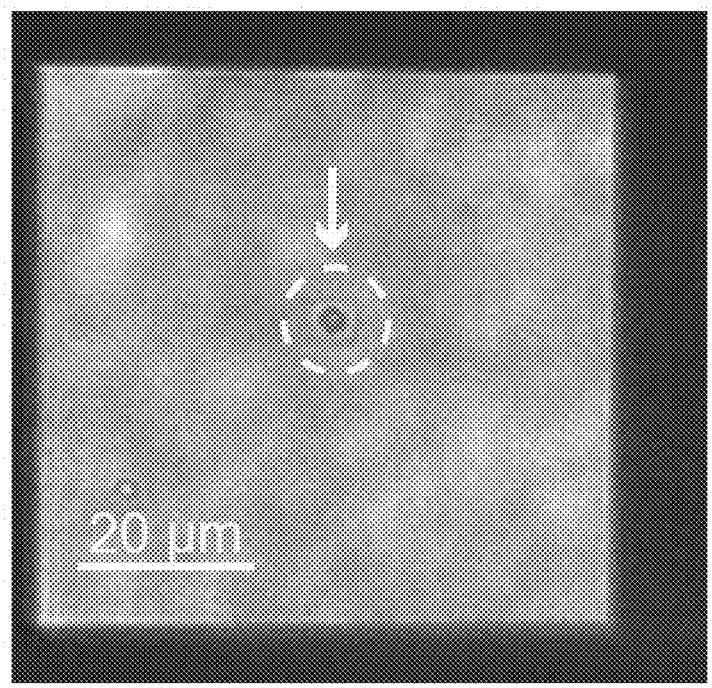
FIG. 5B is an optical microscopy image of DNA trapped in an exemplary device comprising a cavity.
Figure 5C:
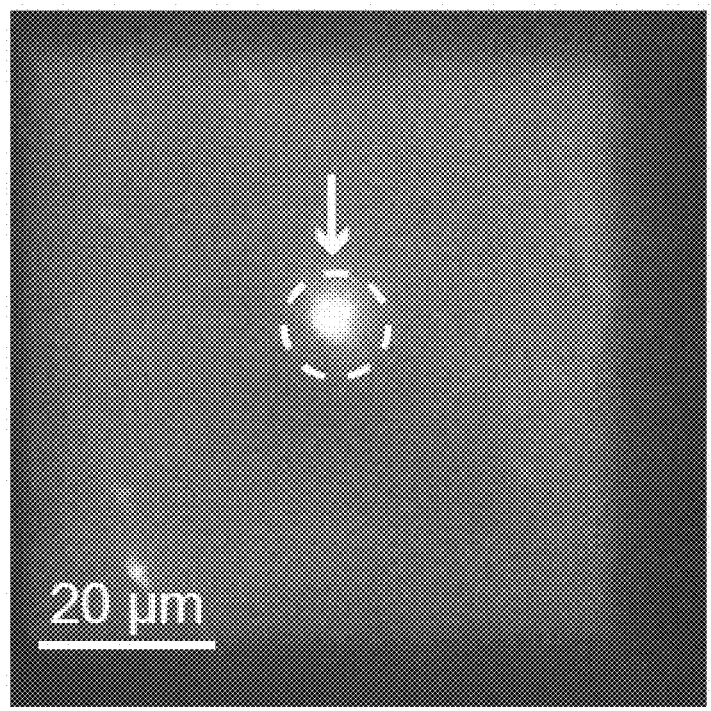
FIG. 5C is a fluorescence optical microscopy image of fluorescently labelled DNA trapped in an exemplary device comprising a cavity.
Figure 5D:
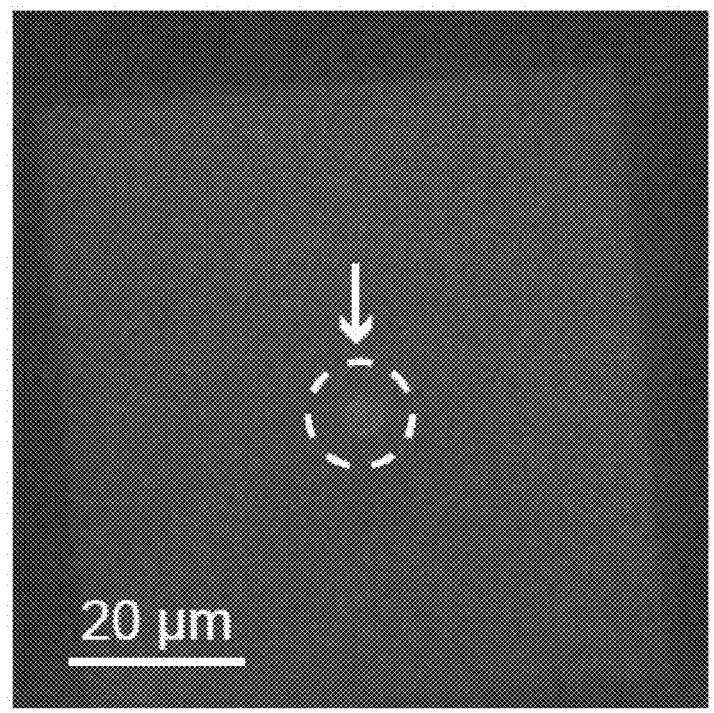
FIG. 5D is a fluorescence optical microscopy image an exemplary device comprising a cavity, in the absence of fluorescently labelled DNA.

The entropic cage stably trapped λ-DNA (lambda DNA) as observed in the following experiments. A voltage was applied across the device to pull a DNA molecule into an entropic cage and left it trapped there. The device was then transferred to an optical microscope, with the opening side facing up, and a drop of solution containing the fluorescent dye YOYO-I was placed onto the chip, as illustrated in FIG. 5A. The YOYO-1 could diffuse through the opening of the cage and stain the DNA molecule inside while the process was observed optically. The cavity was located in white light mode (FIG. 5B) and then that region was monitored in fluorescence mode for about 25 minutes, recording an image every 10 s. A bright spot appeared in the location of the cavity (FIG. 5C), showing that a DNA molecule was trapped inside. This experiment was repeated on two more nanopore devices and the same result was obtained. FIG. 5D shows the results of a control experiment where the ping-pause-pong procedure was used to pull the DNA molecule into the cavity, pause for 5 s, and then remove it before transferring the device to the microscope. As expected, no fluorescence was visible since no molecule was in the cage. The result of this control experiment was reproduced on a second nanopore device.

Example 4

The follow example demonstrates the ability to react entropically trapped DNA with another molecule (e.g., cutting trapped DNA molecules with a restriction endonuclease) in the nanopore/cavity devices described in Example 1.

Figure 6A:
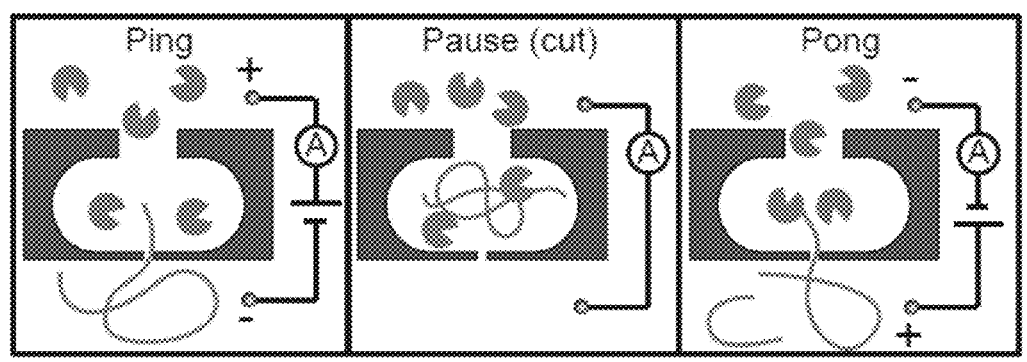
FIG. 6A is a schematic illustration of a "ping, pause, pong" experiment, according to one set of embodiments.

An entropic cage (i.e. device) was used to subject trapped DNA molecules to a sequence-specific biochemical reaction, as illustrated in FIG. 6A. Buffer containing the SmaI restriction endonuclease was added to the reservoir on the opening side, while the reservoir on the nanopore side was filled with a similar buffer that contained λ-DNA (lambda DNA) instead of the enzyme. The ping-pause-pong technique was used to draw a DNA molecule into the cage, where it could interact with SmaI during the pause, and then the voltage was reversed so that the nanopore would interrogate the products of the reaction. SmaI generally cuts double-stranded DNA at a particular recognition sequence found at three sites along λ-DNA (lambda DNA). It was therefore expected a λ-DNA (lambda DNA) molecule entering the cage to be cut into as many as 4 pieces, with the number of pieces increasing as the reaction progresses to completion.

Figure 6B:
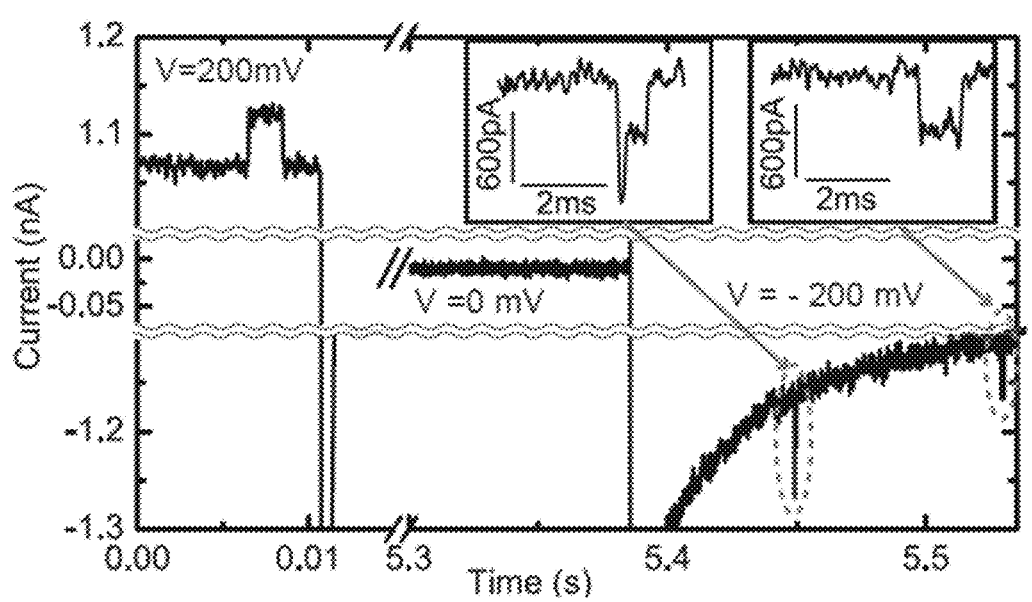
FIG. 6B is a plot of current versus time for an exemplary "ping, pause, pong" experiment.

FIG. 6B shows an exemplary current trace obtained with $t_p=5$ s. Applying V=200 mV drew a DNA molecule into the cage through the nanopore, in this case causing an increase in I, likely due to the highly charged nature of DNA and therefore entrains enough counterions into the nanopore to increase its conductance in low salinity enzyme buffer. After the pause, the voltage was flipped to V=−200 mV and maintained for 5 s. From the single ping, two pong signals were obtained in this case, indicating that a molecule was trapped inside the cavity, cut, and pulled back through in pieces. $t_p$ was varied in our experiments between $t_p=1$ s, 5 s, and 20 s to probe the restriction reaction after different incubation times. At each $t_p$, the experiment was repeated at least 60 times. Control experiments with no SmaI present and $t_p=5$ s were also conducted.

Figure 6C:
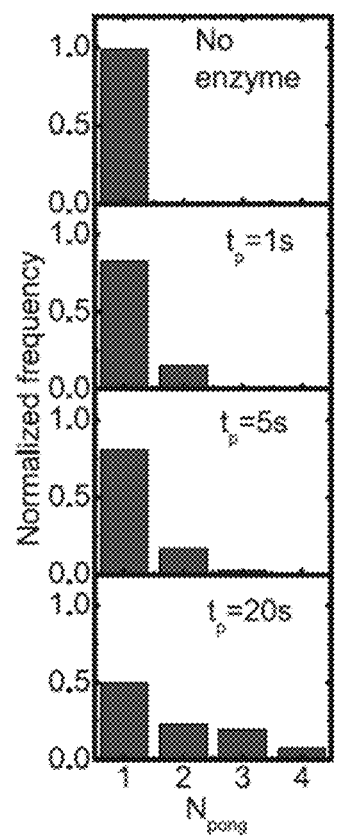
FIG. 6C is a histogram plot of "pongs" for an exemplary "ping, pause, pong" experiment.

FIG. 6C shows the distribution of the number of pongs observed per ping-pause-pong cycle ($N_{pong}$) for the different incubation times and for the experiment with no enzyme. Between 1 and 4 molecules were recaptured per cycle. Without SmaI, 98.6% of the experimental cycles returned only one pong. With SmaI present, the probability of detecting multiple pongs in a cycle increased with $t_p$, from 17.3% at $t_p=1$ s to 50.0% at $t_p=20$ s.

Figure 6D:
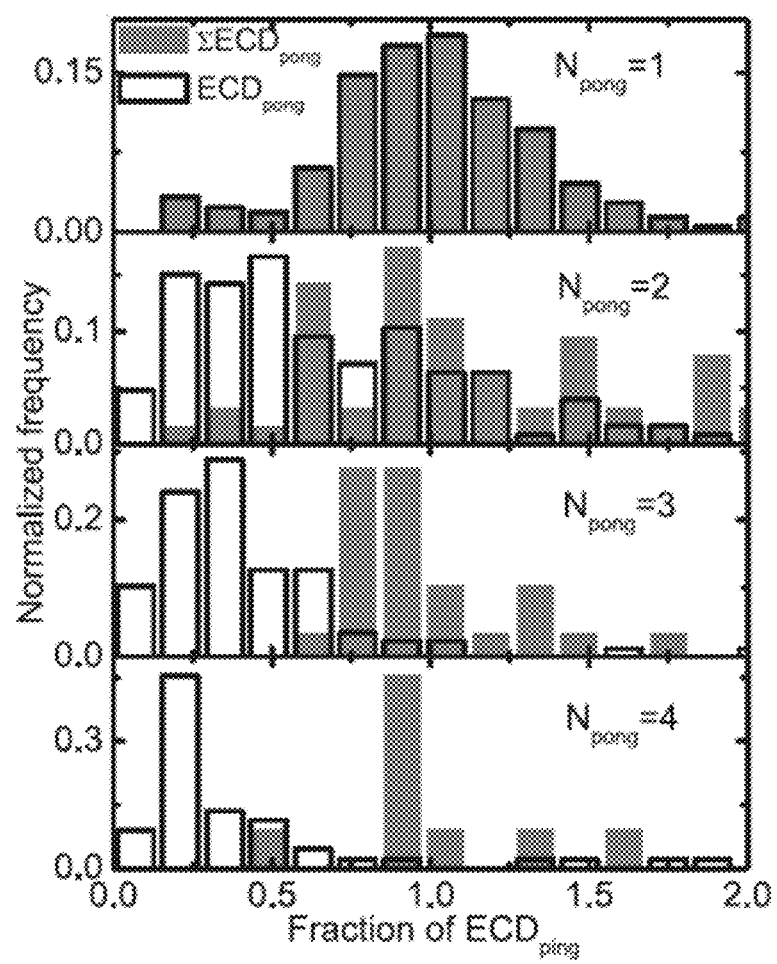
FIG. 6D is normalized histogram plot of ECD for an exemplary "ping, pause, pong" experiment.
Figure 7A:
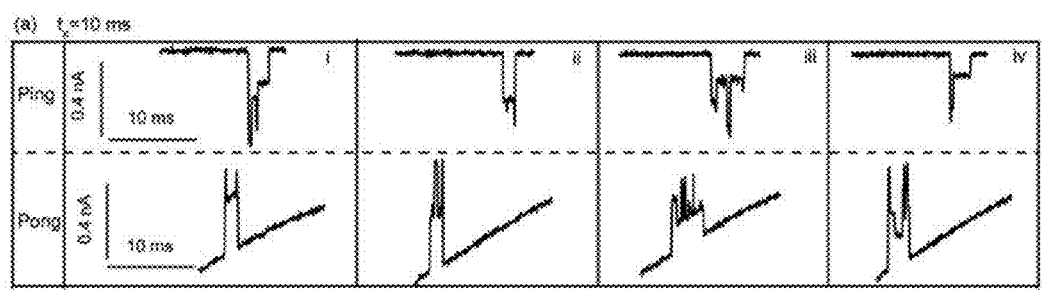
FIGS. 7A-7D are plots of current versus time for exemplary "ping, pause, pong" experiments.
Figure 7B:
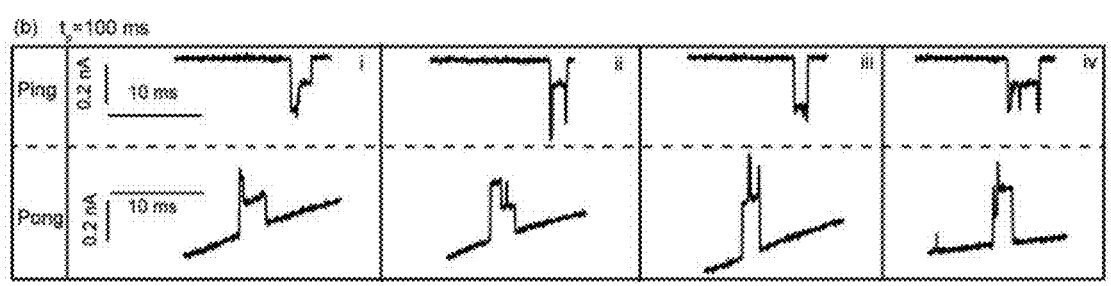
Figure 7C:
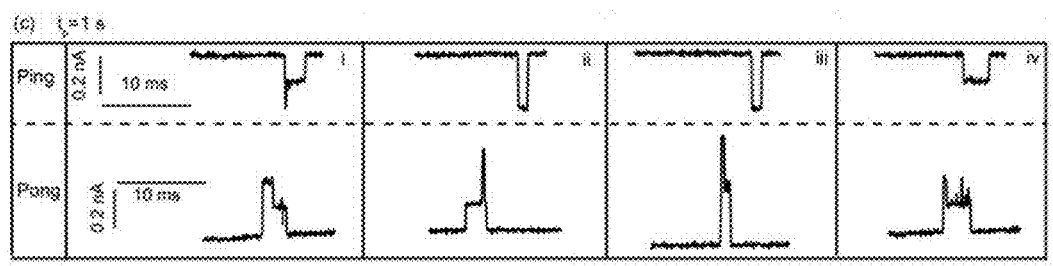
Figure 7D:
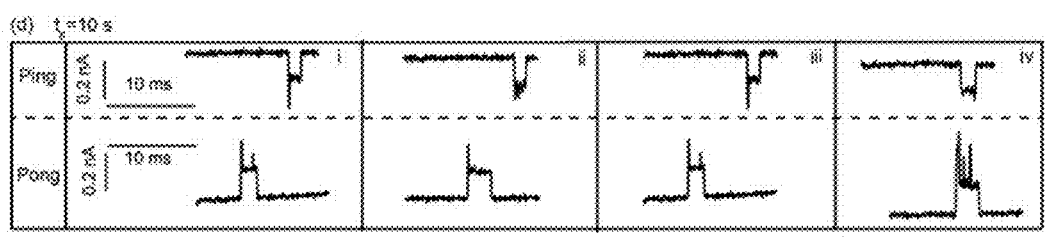
Figure 8A:
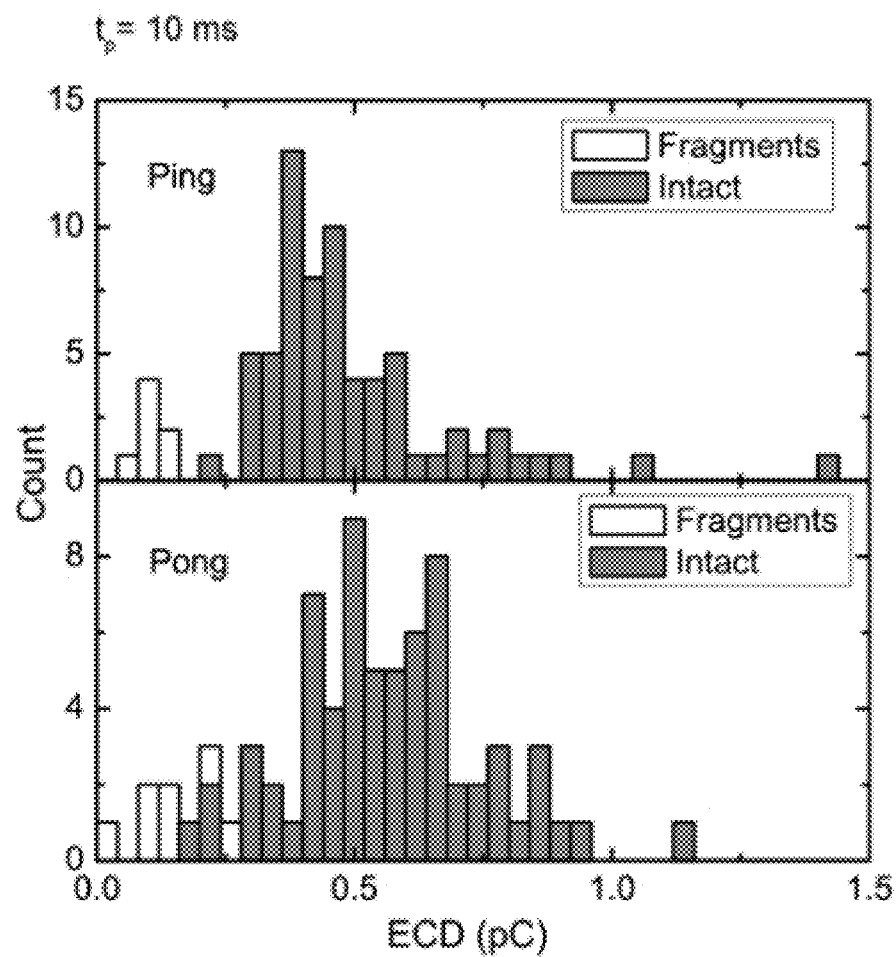
FIGS. 8A-8D are histogram plots of ECD distributions for exemplary "ping" and "pong" experiments.
Figure 8B:
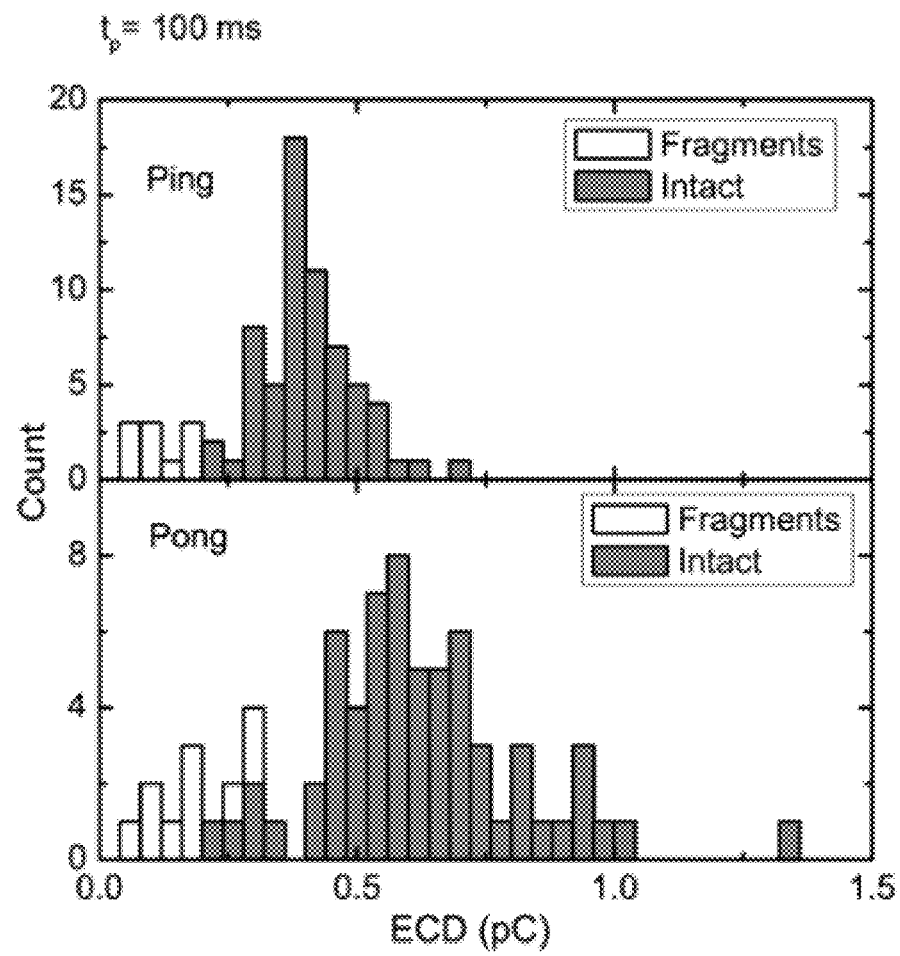
Figure 8C:
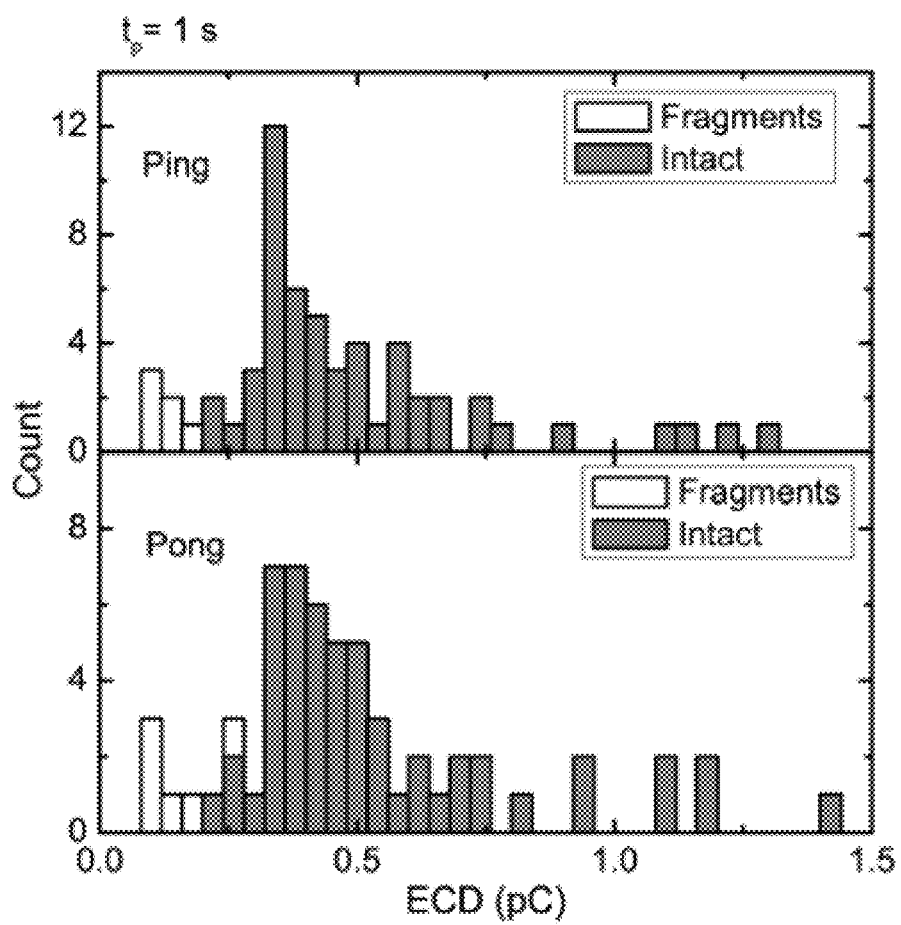
Figure 8D:
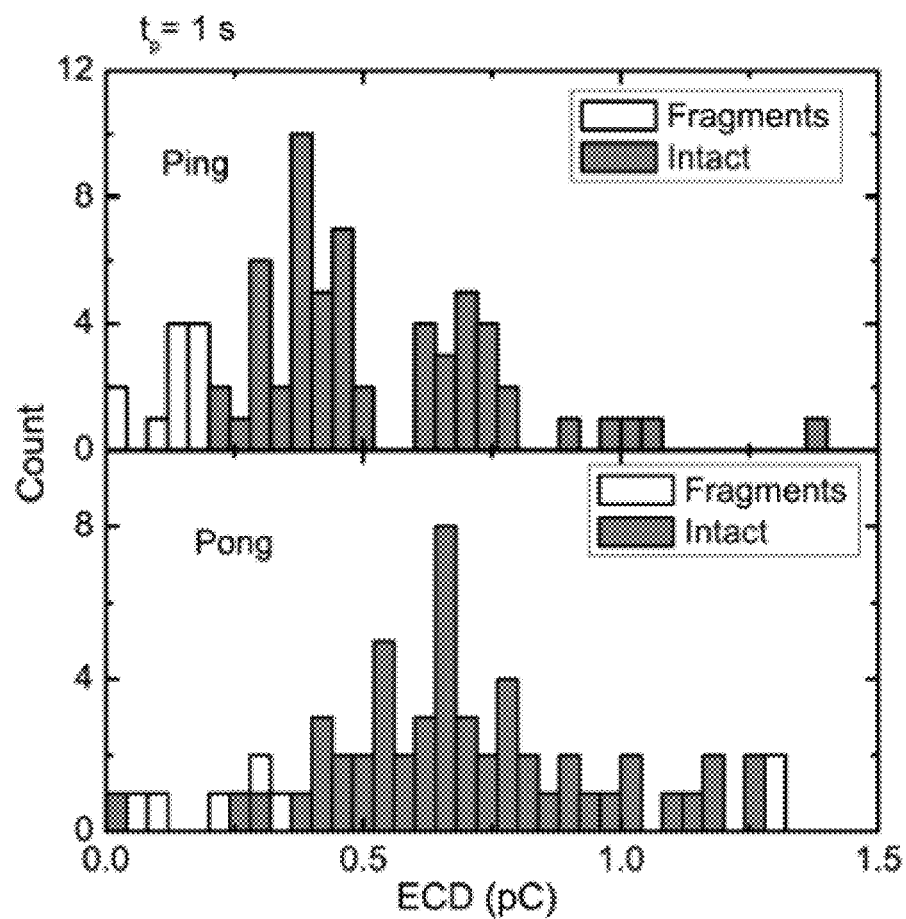

To confirm that multiple pong signals were caused by fragments of the original molecule, it was verified that the fragments were smaller than the original molecule and compared the total size of the recaptured fragments in a cycle with the size of the original molecule, using ECD as a measure of size. FIG. 6D shows the distributions of $ECD_{pong}/ECD_{ping}$, the ECD values of the pongs relative to the corresponding ping, grouped by $N_{pong}$ (white bars). FIG. 6D also plots the distributions of $\Sigma ECD_{pong}/ECD_{ping}$, the total ECD of all the pongs in a cycle relative to the corresponding ping (grey bars). When $N_{pong}=1$, the distribution of $ECD_{pong}/ECD_{ping}$ was centered around 1, indicating that the molecule was not cut because its size did not change. As more pongs were detected per cycle, the distribution $ECD_{pong}/ECD_{ping}$ shifted to lower values, indicating that the recaptured molecules were becoming smaller EcDpm, than the original one. The peak of the $\Sigma ECD_{pong}/ECD_{ping}$ distribution remained near 1 for all $N_{pong}$, however, indicating that the total size of the recaptured molecules was the same as the original.

Figure 11:
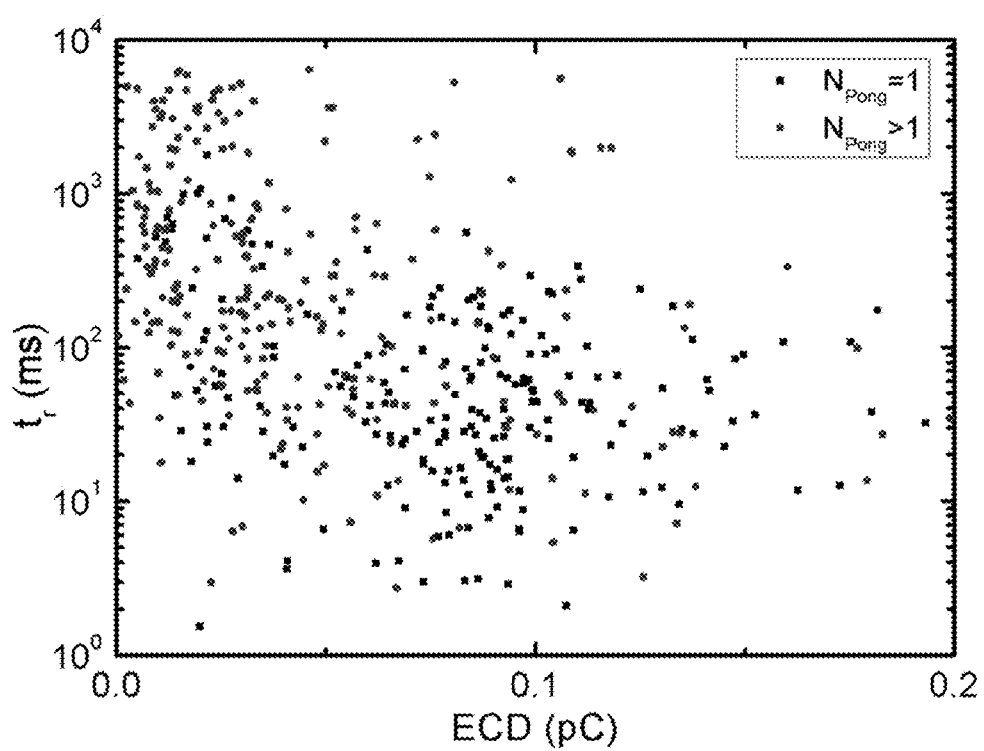
FIG. 11 is a scatter plot sowing the event charge deficit (ECD) for an exemplary set of "pongs" of DNA trapped in a cavity.

It should be noted that since short DNA fragments have a relatively high diffusivity, they can more easily diffuse away from the nanopore against the pull of the electrophoretic force. Fragments consequently exhibited longer recapture times than intact λ-DNA molecules. In the enzymatic cutting experiments, molecules that had not been cut gave pongs in the high ECD, short $t_r$ region of the data, while the fragments produced by the restriction digest gave pongs in the low ECD, long $t_r$ region (see FIG. 11). Similarly, the data in FIG. 4A show that short DNA fragments, as measured by ECD, generally resulted in the longest $t_r$.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the invention includes that number not modified by the presence of the word "about."

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device, comprising:
   a first layer, a second layer adjacent the first layer, and a third layer adjacent the second layer, the second layer comprising a cavity having a largest cross-sectional dimension of between about 2 microns and about 8 microns and being defined between the first layer and the third layer,
   wherein the first layer comprises a nanopore having a largest cross-sectional dimension of less than about 20 nm accessing the cavity, and the third layer comprises a pore having a largest cross-sectional dimension of between about 200 nm and about 6000 nm accessing the cavity.

2. The device of claim 1, further comprising a voltage source capable of generating an electric field across the device.

3. The device of claim 1, wherein the cavity is substantially capsule shaped.

4. The device of claim 1, wherein the first layer comprises silicon nitride.

5. The device of claim 1, wherein the second layer comprises silicon dioxide.

6. The device of claim 1, wherein the third layer comprises silicon nitride.

7. The device of claim 1, wherein the first layer has a thickness of between about 10 nm and about 50 nm.

8. The device of claim 1, wherein the second layer has a thickness of between about 0.5 microns and 5 microns.

9. The device of claim 1, wherein the third layer has a thickness of between about 100 nm and about 1000 nm.

10. The device of claim 1, wherein the nanopore has a volume of less than about 6000 cubic nanometers.

11. The device of claim 1, wherein the cavity has a volume of between about 1 cubic micron and about 15 cubic microns.

12. The device of claim 1, wherein the pore has a volume of between about 0.01 cubic microns and about 10 cubic microns.

13. The device of claim 1, further comprising a first fluid adjacent the first layer.

14. The device of claim 13, further comprising a second fluid adjacent the third layer, wherein the difference in an ionic strength of the first fluid and an ionic strength of the second fluid is at least about 10%.

15. The device of claim 1, wherein the nanopore, cavity, and pore form a fluidic pathway.

16. The device of claim 1, wherein a straight line can be drawn through both the nanopore and the pore without contacting any of the first layer, the second layer, or the third layer.

17. A method, comprising:
   contacting a first fluid having a first ionic strength with a first surface of a device, wherein the first fluid comprises a molecule;
   contacting a second fluid having a second ionic strength with a second surface of the device such that the molecule is urged into a cavity within the device, the cavity having a volume of between about 1 cubic micrometers and about 15 cubic micrometers; wherein the first ionic strength and the second ionic strength are different.

18. The method of claim 17, wherein the device comprises a first layer, a second layer adjacent the first layer, and a third layer adjacent the second layer, the second layer comprising a cavity having a largest cross-sectional dimension of between about 2 microns and about 8 microns and being defined between the first layer and the third layer,
   wherein the first layer comprises a nanopore having a largest cross-sectional dimension of less than about 20 nm accessing the cavity, and the third layer comprises a pore having a largest cross-sectional dimension of between about 200 nm and about 6000 nm accessing the cavity.

19. The method of claim 17, wherein the device comprises a first layer, a second layer adjacent the first layer, and a third layer adjacent the second layer, the second layer comprising a cavity having a volume of between about 1 cubic micron and about 15 cubic microns and being defined between the first layer and the third layer,
   wherein the first layer comprises a nanopore having a volume of less than about 6000 cubic nanometers accessing the cavity, and the third layer comprises a pore having volume of between 0.01 cubic microns and about 10 cubic microns accessing the cavity.

* * * * *